(12) United States Patent
Mittelstadt et al.

(10) Patent No.: US 6,883,518 B2
(45) Date of Patent: Apr. 26, 2005

(54) UNIDIRECTIONAL RESPIRATOR VALVE (75) Inventors: William A. Mittelstadt, Woodbury, MN (US); David M. Castiglione, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 213 days.

(21) Appl. No.: 09/888,732

(22) Filed: Jun. 25, 2001

(65) Prior Publication Data

US 2002/0195108 A1 Dec. 26, 2002

(51) Int. Cl.[7] .......................... A62B 18/08; A62B 23/02; A62B 7/10
(52) U.S. Cl. ............................ 128/206.15; 128/205.24; 128/206.21; 128/205.25
(58) Field of Search ..................... 128/206.15, 205.24, 128/206.21, 205.25, 206.13, 207.17, 201.28, 207.12, 205.27, 205.29, 206.12, 206.28, 207.16; 337/885; 137/533.17

(56) References Cited

U.S. PATENT DOCUMENTS

| | | | |
|---|---|---|---|
| 2,378,613 A | * 6/1945 | Young et al. | ................ 137/855 |
| 2,999,498 A | 9/1961 | Matheson | |
| 3,085,591 A | 4/1963 | Schneider | |
| 3,990,439 A | * 11/1976 | Klinger | ................ 128/207.12 |
| 4,414,973 A | 11/1983 | Matheson et al. | |
| 4,630,604 A | 12/1986 | Montesi | |
| 4,850,346 A | 7/1989 | Michel et al. | |
| 4,934,362 A | 6/1990 | Braun | |
| 4,958,633 A | 9/1990 | Angell | |
| 4,974,586 A | 12/1990 | Wandel et al. | |
| 4,981,134 A | 1/1991 | Courtney | |
| 5,160,322 A | * 11/1992 | Scheremet et al. | ......... 128/887 |
| 5,231,982 A | * 8/1993 | Harrison et al. | ....... 128/201.28 |
| 5,325,892 A | 7/1994 | Japuntich et al. | |
| 5,509,436 A | 4/1996 | Japuntich et al. | |
| 5,584,288 A | * 12/1996 | Baldwin | ................ 128/202.28 |
| 5,662,142 A | 9/1997 | Ansite | |
| 5,687,767 A | 11/1997 | Bowers | |
| 5,813,401 A | 9/1998 | Radcliff et al. | |
| 5,829,433 A | * 11/1998 | Shigematsu et al. | ... 128/202.28 |
| D413,166 S | 8/1999 | Snow et al. | |
| 6,047,698 A | 4/2000 | Magidson et al. | |
| 6,070,574 A | * 6/2000 | O'Day et al. | .......... 128/202.28 |
| 2002/0023651 A1 | * 7/1998 | Japuntich et al. | ....... 128/206.15 |

FOREIGN PATENT DOCUMENTS

| | | |
|---|---|---|
| DE | 1213249 | 3/1966 |
| EP | 0 252 890 | 1/1988 |
| EP | 0 252 891 | 1/1988 |
| FR | 2020438 | 7/1970 |

OTHER PUBLICATIONS

7700 Series Half Mask Respirators, Pro—Am, 2000, available at http://www.pro—am.com/CAtalog/Exec/product.asp?product_id=64.*

* cited by examiner

Primary Examiner—Henry Bennett
Assistant Examiner—Andrea M. Ragonese
(74) Attorney, Agent, or Firm—Michaele A. Hakamaki; Karl G. Hanson; Kevin W. Raasch (57) ABSTRACT

A unidirectional valve, wherein the valve comprises a valve body including a frame, a valve opening through the frame, and a valve seat extending from the frame and at least partially surrounding the valve opening. The valve further includes a valve flap having a first portion attached to the frame and an adjacent second portion free to move from a first position where the second portion is in contact with at least a part of the valve seat to a second position where at least part of the second portion is spaced from the valve seat, wherein the valve flap has a nonuniform thickness. The thickness variations may occur between sides of the valve flap, and may also occur between the ends of the valve flap.

35 Claims, 4 Drawing Sheets

UNIDIRECTIONAL RESPIRATOR VALVE

TECHNICAL FIELD

The present invention relates to respirator equipment for protecting the breathing zone of users from gases, vapors, and particulates. More particularly, the present invention provides a valve for use with such respirators.

BACKGROUND OF THE INVENTION

Various types of respirators are commonly worn by people who work in areas where the air may be contaminated with toxic or noxious substances such as airborne particulates, gases, and vapors. The type of respirator used in a particular environment depends on the amount and type of protection required by the wearer.

One general category of respirators typically includes those having a breathing mask with at least one filtered air inlet and at least one exhalation outlet or port. These respirators may be of the type referred to as half facepiece respirators, which typically cover the mouth and nose of the wearer, or of the type referred to as full facepiece respirators, which additionally cover the face and eyes of the wearer. With these types of respirators, the wearer pulls air through the filtered air inlet or inlets by drawing a breath, thereby creating a negative pressure in the mask. When the wearer exhales, the air released from the wearer's mouth creates a positive pressure in the mask, causing the air to exit the mask through the exhalation outlet or port when the positive air pressure reaches a certain level.

Another general type of respirator is referred to as a filtering facemask, which generally includes a mask body made of a filtering material that is permeable to air. The facemask may additionally include at least one exhalation outlet or port. This type of respirator typically covers the mouth and nose areas of the wearer. When in use, the wearer inhales and pulls air through the permeable mask material, then exhales and pushes air out of the facemask through the exhalation valve or port.

The components used for a particular respirator should not make breathing difficult for the wearer and ideally should allow the wearer to inhale and exhale comfortably when using the respirator. Respirator components that can affect the comfort of the respirator wearer are the valves, which may include both exhalation and inhalation valves. An exhalation valve selected for a respirator should allow a high percentage of air to easily escape from the interior portion of the breathing mask when the wearer exhales so that air pressure does not build up inside the mask. This can be accomplished by providing a valve portion that is displaced relatively easily from its valve seat when the wearer exhales. However, the valve portion also should seal easily against the valve seat when the wearer is not exhaling so that contaminated or unfiltered air does not unintentionally leak into the wearer's breathing zone. Although an inhalation valve would similarly allow for passage of air through the valve, it would typically be positioned in the opposite orientation from an exhalation valve. In this way, a valve portion would be displaced from its valve seat when the wearer inhales. It is also desirable that any valves provide the same protection to the wearer regardless of the orientation of the respirator.

SUMMARY OF THE INVENTION

In one aspect of this invention a unidirectional valve is provided, wherein the valve comprises a valve body including a frame, a valve opening through the frame, and a valve seat extending from the frame and at least partially surrounding the valve opening. The valve further includes a valve flap having a first portion attached to the frame and an adjacent second portion free to move from a first position where the second portion is in contact with at least a part of the valve seat to a second position where at least part of the second portion is spaced from the valve seat, wherein the valve flap has a nonuniform thickness. The thickness variations may occur between sides of the valve flap, and may also occur between the ends of the valve flap.

In another aspect of this invention, a respirator is provided having a unidirectional valve, the respirator comprising a face mask having at least one opening for receiving a unidirectional valve, wherein the unidirectional valve comprises a valve body including a frame, a valve opening through the frame, and a valve seat extending from the frame and at least partially surrounding the valve opening. The valve flap has a first portion attached to the frame and an adjacent second portion free to move from a first position where the second portion is in contact with at least a part of the valve seat to a second position where at least part of the second portion is spaced from the valve seat, wherein the valve flap has a nonuniform thickness.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF THE PREFERRED EMBODIMENTS

Figure 1:
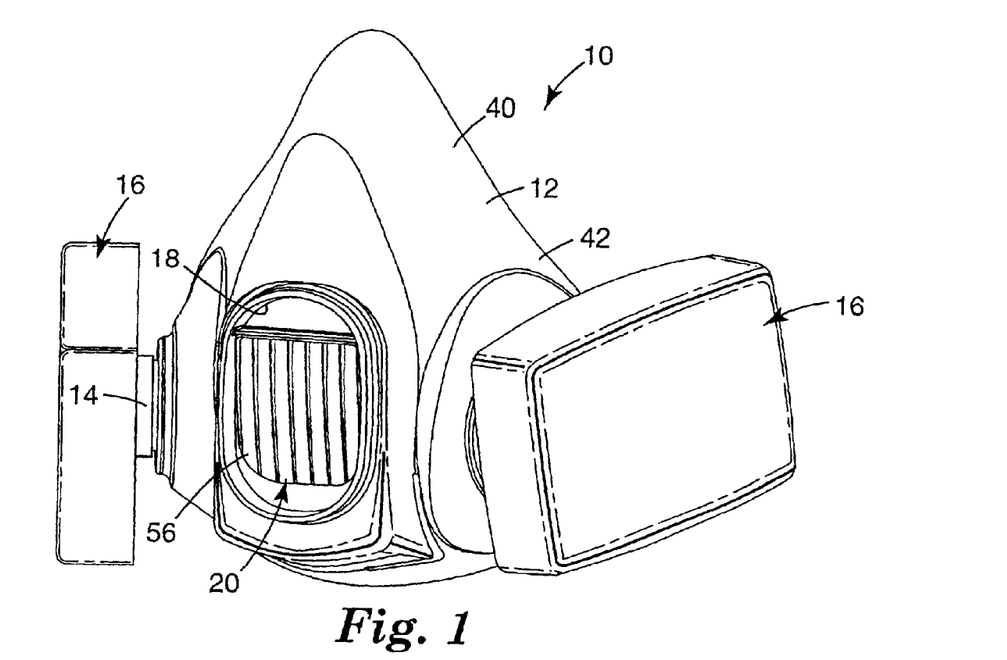
FIG. 1 is a perspective view of a respirator in accordance with the present invention.
Figure 2:
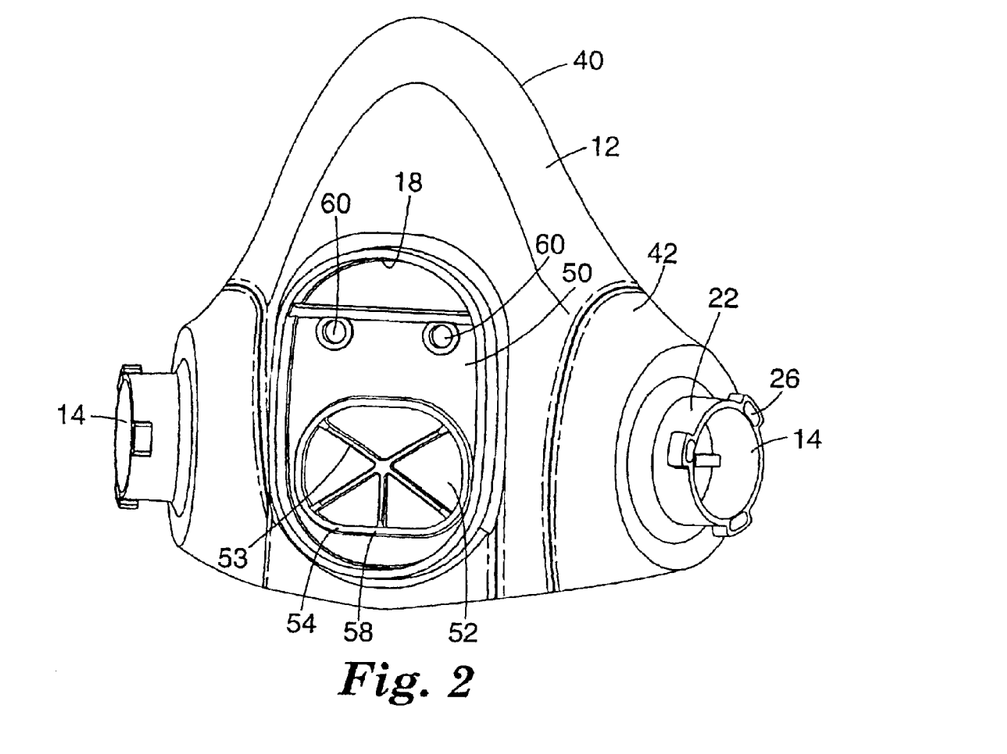
FIG. 2 is a perspective view of a respirator similar to that of FIG. 1, with certain components omitted.

Referring now to the Figures, wherein the components are labeled with like numerals throughout the several Figures, and initially to FIGS. 1 and 2, one embodiment of an air purifying respirator 10 is illustrated, which is generally of the type referred to as a half facepiece respirator. Respirator 10 includes a flexible face piece 12 having two openings or ports 14 to which air inlet assemblies 16 are fitted or secured, and an opening 18 to which an exhalation valve assembly 20 is fitted or secured. As shown, air inlet assemblies 16 are positioned on opposite sides or ends of face piece 12 and are positioned low on the face piece so as to not obstruct the view of a person wearing the respirator. Opening 18 is located in the central area of the face piece 12 so that it is generally in front of the mouth or breathing zone of the wearer. Each of the openings 14, 18 extend into the interior area of face piece 12.

Air inlet assemblies 16 can comprise chemical cartridges, air lines, particulate filters, or other various components. Assemblies 16 may also include a combination of several components to achieve specific qualities of the air entering a wearer's breathing space. In one aspect of the invention, openings 14 are generally cylindrical in shape and each has a circular flange 22 that extends outwardly from face piece 12. Each of these flanges 22 is designed to receive a mating fitting (not shown) of one of the air inlet assemblies 16 to allow for secure attachment of the assemblies 16 to the face piece 12. For the aspect shown, flange 22 has three tabs 26 that are designed to engage with a channel (not visible) on the mating fitting. The inside diameter of the mating fitting is slightly larger than the outer diameter of flange 22 so that the pieces can fit securely together without interfering with each other during attachment of assemblies 16. To secure an assembly 16 to a flange 22, the mating fitting is slid over flange 22 until the tabs 26 engage with a channel on the inside that fitting. The assembly 16 is then rotated until the tabs 26 lock into place in the channel. This design allows for relatively easy detachment of assemblies 16 from flanges 22 when desired. However, it is understood that any of a number of alternate configurations may be used to secure the assemblies 16 to the face piece 12, where the assemblies 16 may be removable and replaceable, or may be permanently secured. While the above described method of attachment does not require additional tools for attaching and removing the air inlet assemblies, other attachment methods may require tools.

Face piece 12 comprises a nose portion 40 that extends from the upper portion of a body portion 42. Body portion 42 is shaped to conform generally to the shape of a wearer's face, and is at least partially convex in shape. The body and nose portions 40, 42 should be large enough so that the face piece material is positioned at a comfortable distance from the wearer's face when in use, but should be small enough to provide a secure fit between the face piece 12 and the wearer's face. The size and shape of the nose and body portions 40, 42 may vary widely, depending on the particular aesthetic and functional requirements of the respirator.

Face piece 12 may be made of any of a variety of materials, including flexible materials such as silicone, rubber, or thermoplastic elastomers, such as those commercially available under the trade designations "Kraton" from Shell Oil of Houston, Tex., "Monprene" from Teknor Apex of Pawtucket, R.I., and "Santoprene" from Advanced Elastomer Systems of Akron, Ohio. However, a wide range of materials with various flexibilities would be appropriate for face piece 12.

As discussed above, exhalation valve assembly 20 is fitted in opening 18 of face piece 12, as is illustrated in FIGS. 1 and 2, where FIG. 2 shows the valve assembly 20 without some of its components to better view the various features of the assembly. Exhalation valve assembly 20 generally includes a frame 50 having an opening or orifice 52, a valve seat 54 extending generally around the periphery of opening 52, and a valve diaphragm 56. Opening 52 can further include support members 53 that can provide reinforcement and stabilize the frame 50. The support members 53 can further prevent valve diaphragm 56 from being pulled through opening 52 and into the interior area of face piece 12 during air pressure changes.

Opening 52 is shown as a partially flattened oval in shape, however, any number of shapes would be possible. Valve seat 54 may closely match the size and shape of the periphery of opening 52, or may have a different size and/or shape than opening 52. In one aspect of the invention, the opening 52 has the same general outer periphery size and shape as the size and shape of the periphery of the inside of valve seat 54. In any case, valve seat 54 has a top surface 58 which can be generally smooth or may be textured, where the smoothness of top surface 58 can affect the level of sealing achieved between valve diaphragm 56 and top surface 58. Frame 50 further includes two attachment holes 60, which will be further discussed below. As shown, attachment holes 60 are located above the valve seat 54, thereby providing an attachment point for valve diaphragm 56 that is outside the opening 52.

Figure 3:
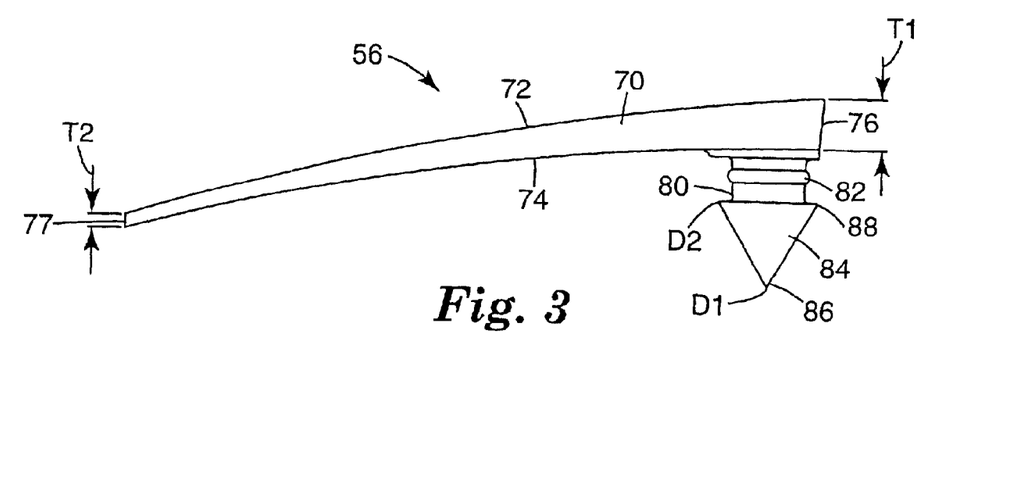
FIG. 3 is a side view of a valve diaphragm in accordance with the present invention.
Figure 4:
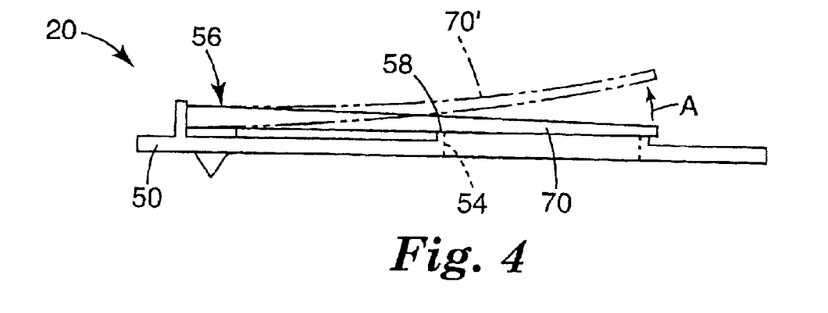
FIG. 4 is a side view of the valve assembly of FIG. 1.

Additionally referring to FIGS. 3 and 4, one embodiment of valve diaphragm 56 is shown, where diaphragm 56 includes a flap portion 70 having a top surface 72, a bottom surface 74, a first end 76, and a second end 77. In this embodiment, flap portion 70 has a constant curvature that extends from first end 76 to second end 77 and the top surface 58 of valve seat 54 defines an essentially flat plane. When the diaphragm 56 is installed on frame 50, the curvature of flap portion 70 toward valve seat 54 creates a bias in flap portion 70 such that the curve of at least a portion of flap portion 70 may flatten or straighten to some degree as it comes in contact with top surface 58 of valve seat 54. In one aspect of the invention, the bias created by the curvature of flap portion 70 is substantial enough to keep flap portion 70 sealed against top surface 58 in all orientations.

Alternatively, flap portion 70 may have a side profile that does not include a constant curvature. For example, the curvature of flap portion 70 may vary from first end 76 to second end 77. Many other variations of the side profile of flap portion 70 are also considered to be with the scope of this invention, where the creation of a bias of the flap portion 70 toward valve seat 54 helps to keep flap portion 70 in a sealed position when it is not subjected to external forces such as air pressure changes.

Flap portion 70 may vary in thickness from first end 76 to second end 77. For one example, flap portion 70 has a thickness T1 at first end 76 that is greater than its thickness T2 at second end 77. The thickness of flap portion 70 may taper gradually from first end 76 to second end 77, as shown, or the thickness can vary less gradually, such as in a type of "step" arrangement. Thickness T1 may alternatively be smaller than thickness T2. Variations in the thickness of flap portion 70 from one end 76 to the other end 77 may be chosen to achieve certain performance characteristics of the valve diaphragm 56, such as a desired amount of force needed to move the flap portion from its closed position to its open position. For example, the flap portion thickness may be smaller in areas where it would be desirable to decrease the force necessary to move the flap portion 70 from one position to another. A wide range of thickness variations are contemplated by the present invention, however, in one aspect of the invention, a difference in the thickness at any point between first end 76 and second end 77 of greater than about 10% is desirable.

Two connectors 80 extend from the bottom surface 74 of flap portion 70, which are used for attachment of diaphragm 56 to frame 50. Connectors 80 include a protrusion 82 and a tapered cap 84, where the cap 84 tapers from a first end 86 having a diameter D1 (which is essentially a point in this example) up to a second end 88 that has a diameter D2 that is greater than the diameter D1 of first end 86. In this aspect of diaphragm 56, both the flap portion 70 and connectors 80 are made of a relatively flexible material. Connectors 80 are designed to be received by attachment holes 60, where the diameter D2 of second end 88 of cap 84 is larger than the diameter of the attachment hole 60 in which it is to be received. In order to engage each connector 80 with its respective attachment hole 60, cap 84 is pressed or pulled into the hole 60 until the outside diameter of cap 84 matches the inside diameter of the hole 60. Additional force is then applied to the connector to temporarily compress and deform cap 84 until second end 88 passes through hole 60. At this point, the connector 80 is positioned so that the flap portion 70 is on one side of frame 50, the protrusion 82 is positioned within the hole 60, and the tapered cap 84 is on the opposite side of frame 50, thereby securing diaphragm 56 to frame 50. To remove a diaphragm 56 from a frame 50, each connector 80 would be pushed or pulled in the opposite direction through its respective hole 60.

The above discussion of the use of connectors to attach a diaphragm 56 to frame 50 is only one of many types of attachment methods contemplated by the present invention. The attachment method chosen for a particular application may provide for either temporary or permanent attachment of diaphragm 56 to frame 50, although a temporary attachment method can allow for removal and replacement of diaphragms as desired. The diaphragm 56 may be secured to frame 50 by any of a number of known attachment methods, including the use of connectors extending from a surface of flap portion 70 that have a different configuration than the connectors 80 described above. It is also understood that more or less than two connectors 80 may be used for a particular valve diaphragm. Alternatively, the diaphragm 56 may be attached to frame 50 through the use of repositionable or permanent adhesives, hook and loop type fasteners, screws or other mechanical fasteners, welding, or other suitable attachment methods. In any of these attachment methods, the flap portion 70 and the attachment devices or materials may be made of the same or different materials. For one example, the flap portion may be made of a thermoset elastomer and attached to a frame by a metal screw or rivet. For another example, the entire valve diaphragm 56, including the flap portion and attachment means, may be made of a single material.

In another aspect of the invention, diaphragm 56 is integrally molded to the frame 50 so that it is not detachable and replaceable from frame 50. In this embodiment, the frame 50 and diaphragm 56 could be removable and replaceable as an integral unit from the face piece 12, if desired.

Figure 5:
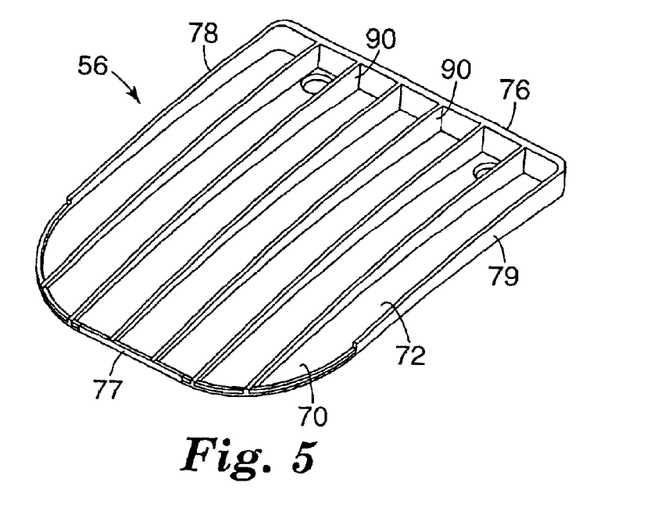
FIG. 5 is a perspective view of another aspect of a valve diaphragm.

Referring now to FIG. 5, one aspect of diaphragm 56 includes multiple ribs 90 extending from the top surface 72 of flap portion 70 for at least part of the distance from the first end 76 to second end 77. In this embodiment, the base part of flap portion 70 has a uniform thickness. The ribs 90 provide additional stiffness to the diaphragm 56, which can be useful in providing the desired seal between the flap portion 70 and the valve seat 54 while minimizing the mass added to the flap portion 70. Further, a flap portion with ribs can have less mass than flap portions that are relatively thick across their entire profile, while achieving the same level of stiffness. In other words, the ratio of stiffness of the flap portion to the mass of the flap portion can be greater by adding ribs than by increasing the thickness across the entire flap portion. When the stiffness to mass ratio of a flap portion 70 is higher, the preload force or amount of bias required to keep valve diaphragm 56 sealed against valve seat 54 would be lower. In addition, the force required to open a particular valve diaphragm having a high stiffness to mass ratio can be lower than the force required to open a valve diaphragm having a low stiffness to mass ratio.

The length, width, and thickness of each rib 90 can be chosen to achieve the desired level of stiffness for the flap portion 70. A single rib 90 or multiple ribs 90 may be used, where the design of each rib 90 may be the same or different than other ribs 90 on the same flap portion 70. Each rib 90 may also vary from one end of the rib to the other end of the rib. For example, each rib 90 may be wider or thicker at one end of that rib than at the other end of that rib. The rib or ribs may also extend for only part of the distance between the first end 76 of flap portion 70 to second end 77. In any case, the number, size, and shape of ribs used should provide a desired level of stiffness to the valve diaphragm while allowing enough flexibility so that the valve diaphragm can open under normal pressure changes.

As discussed above, flap portion 70 may vary in thickness from one end to the other. Flap portion 70, which further includes a first side 78 and a second side 79 in at least one aspect of the invention, may also vary in thickness from side 78 to side 79. For one example, flap portion 70 can have a thickness at first side 78 that is different than the thickness at second side 79. The thickness of flap portion 70 may taper gradually from first side 78 to second side 79 or the thickness can vary less gradually, such as in a type of "step" arrangement, or in any other regular or irregular variation from one side to the other. Further, the inclusion of at least one rib on a particular flap portion may also be considered to be a thickness variation across that flap portion.

Figure 6A:
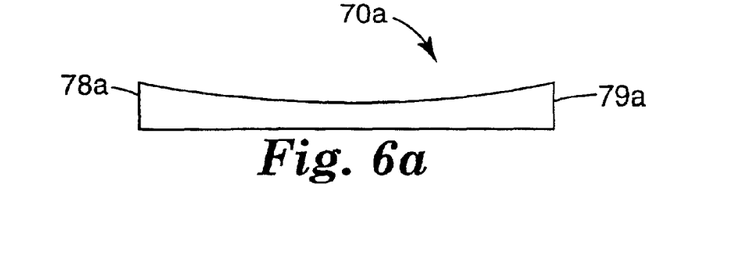
FIGS. 6a and 6b are front views of valve diaphragms in accordance with the present invention.
Figure 6B:
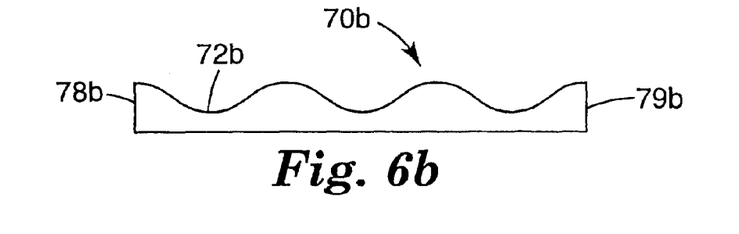

FIG. 6a shows an end view of a flap portion 70a, where the flap portion is thickest near first side 78a and second 79a and thinnest near the middle of the flap portion 70a. Another example of varying the thickness of a flap portion is illustrated in FIG. 6b. As shown, the top surface 72b of the flap portion 70b varies in a sinusoidal pattern from the first side 78b to second side 79b, thereby providing portions of flap portion 70b with different thicknesses. It is understood that any number of thickness variations, both regular and irregular, across the surface of a particular flap portion are possible and are considered to be within the scope of the present invention. In one aspect of the invention, however, a difference in the thickness at any point between the first side 78 and the second side 79 of greater than about 10% is desirable. Like the addition of ribs to a flap portion, these thickness variations can also provide an increased stiffness to mass ratio for a flap portion as compared to a flap portion with uniform thickness from side to side.

One aspect of valve diaphragm 56 includes a flap portion 70 made of a thin membrane or film of relatively flexible material such as silicone, rubber, or a thermoplastic elastomer, for example. A wide variety of flexible materials may be suitable for flap portion 70, where the material is selected to provide the desired level of stiffness to keep the diaphragm 56 sealed against the valve seat 54 when diaphragm 56 is in its closed position, yet provide the desired level of flexibility to allow diaphragm 56 to move away from the valve seat 54 to an open or semi-open position. When valve diaphragm 56 includes additional elements on the top surface 72 of flap portion 70 (such as ribs 90, for example), the additional elements may be the same material as or a different material from the flap portion 70. For example, the additional elements may be made of a material such as a thermoplastic elastomer, plastic, metal, or composite. Again, the material for these components would be selected to provide the desired level of stiffness for a particular diaphragm 56.

Flap portion 70 may further have a shape or "footprint" such as that shown in FIG. 5, where first end 76 is generally parallel to second end 77 and first side 78 is generally parallel to second side 79, however many other shapes for flap portion 70 are possible. The selection of the flap portion shape will depend on the shape and arrangement of the other valve and respirator components and also on the performance characteristics desired for each particular valve assembly.

The flap portion 70 may be manufactured using any method that provides the desired shape, size and curvature of the flap portion. For one example, the flap portion 70 can be molded using standard molding techniques, such as compression molding or injection molding. For another example, flap portion 70 can be extruded to form a particular profile from either the side or the end of the flap portion 70, which is sometimes referred to as profile extrusion.

In operation, valve diaphragm 56 rests or seals against valve seat 54 when in its closed position, where a better seal is typically achieved when more of the surface area of the valve seat 54 comes in contact with a corresponding portion of the valve diaphragm 56. An illustration of valve diaphragm 56 with its flap portion 70 in a closed position is shown in FIG. 4 in solid lines. When flap portion 70 has a curvature as described above, this curve would be at least partially flattened out onto a valve seat 54 that is generally planar, as illustrated. In this way, the valve diaphragm 56 is preloaded with the curvature of the flap portion 70, which provides the necessary sealing force to keep the valve diaphragm 56 in its closed position when not subjected to other forces. When the wearer exhales air, the air pressure inside respirator 10 increases until the pressure becomes sufficiently high that the valve diaphragm 56 is forced away from the valve seat 54 in the direction shown by arrow A. With a certain amount of pressure that depends on the particular respirator components used, the flap portion will be displaced into the position shown by broken lines and indicated by reference number 70'.

In one aspect of the invention, connectors 80 are located closer to the first end 76 of flap portion 70 than the second end 77. When the valve assembly 20 is assembled, the valve diaphragm 56 is thus supported in a cantilever style arrangement, where the area of the diaphragm 56 closest to first end 76 is secured to the frame 50 so that its movement is limited relative to frame 50, while the area of the diaphragm 56 closest to second end 77 has more freedom to move relative to frame 50. This arrangement allows the valve diaphragm to move from an open position to a closed position, depending on the breathing action of the wearer. When the diaphragm 56 is secured to frame 50 at its furthest point from the free end 77 of the flap portion 70, the longest possible moment arm is created. The moment arm for this aspect of the invention is defined as the distance from the attachment point of the flap portion 70 to the free end of the flap portion that is furthest from the attachment point. In this way, for a given pressure, the opening distance of the second end 77 of flap portion 70 from valve seat 54 is greater than if the moment arm were shorter.

In another aspect of the invention, the flap portion 70 would have an intermediate connector or connectors that would secure to the frame 50 so that two or more cantilever style flaps are created on either side of the connector or connectors. In this type of arrangement, the opening in the face piece may have an intermediate supporting structure to which the connector or connectors can attach, or there may actually be two or more openings or orifices in the front part of the face piece. Each of the multiple cantilever style flaps would preferably be positioned over an opening or orifice for sealing thereof.

Figure 7:
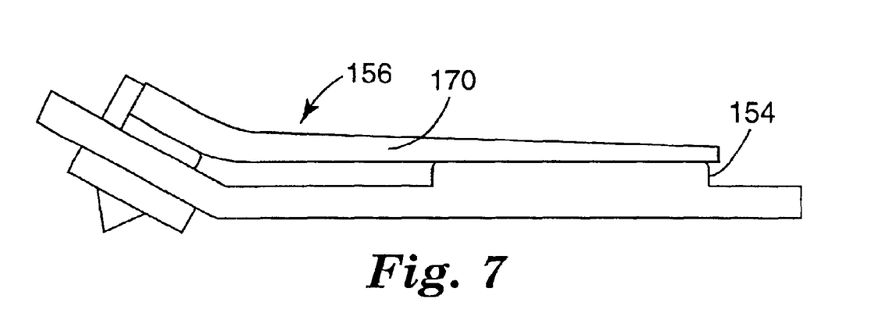
FIG. 7 is a side view of another valve assembly of the invention.

In another aspect of the present invention shown in FIG. 7, a valve diaphragm 156 is provided with a flap portion 170 that is a flat or planar piece. In this aspect, the diaphragm 156 is attached at an angle relative to the generally flat plane of valve seat 154, thereby bending the flap portion 170 relative to the valve seat 154 and providing the necessary preload or bias to keep the valve diaphragm in its closed position when the respirator is not subject to pressure changes. The diaphragm 156 may have any of the thickness or profile variations discussed above relative to valve diaphragm 56.

Figure 8:
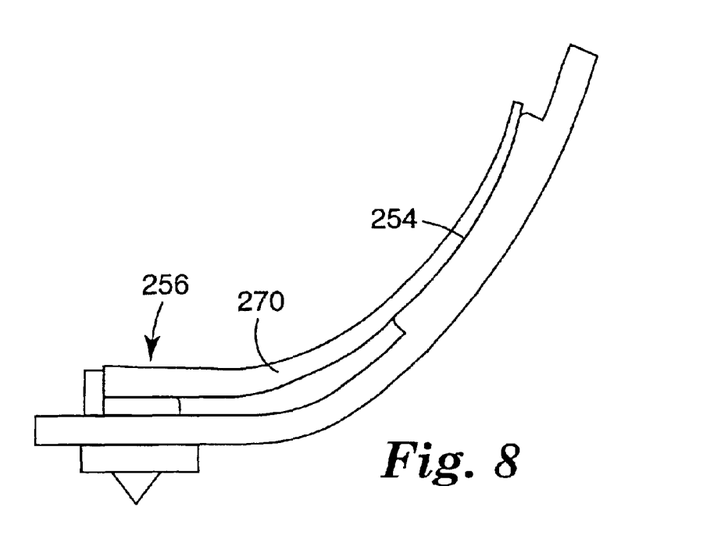
FIG. 8 is a side view of another valve assembly of the invention.

Alternatively, valve diaphragm 256 may be provided with a flap portion 270 that is a flat or contoured piece and the valve seat 254 is not planar, as shown in FIG. 8. In this aspect of the present invention, the curvature of valve seat 254 creates the necessary preload to keep the valve diaphragm 254 in its closed position when desired. Again, valve diaphragm 256 may have any of the thickness or profile variations previously discussed relative to valve diaphragm 56.

Figure 9:
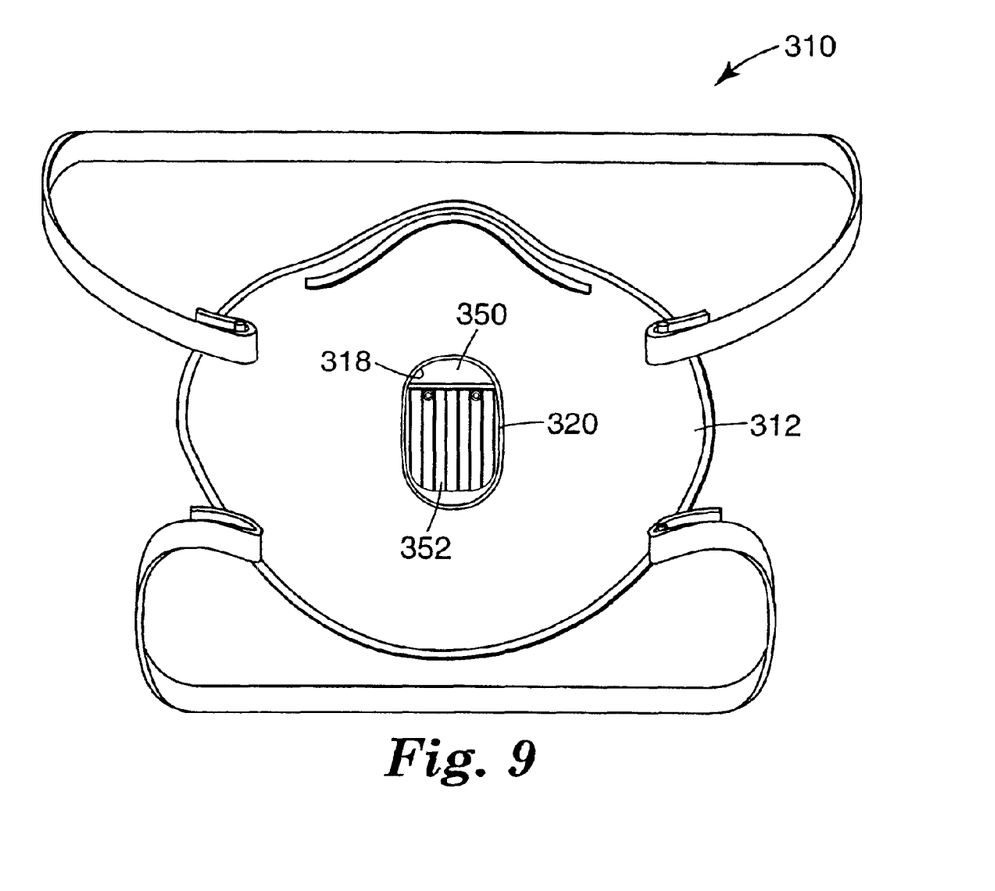
FIG. 9 is a perspective view of another respirator arrangement in accordance with the present invention.

While the above description is directed to a half facepiece type respirator, the valve of the present invention is not intended to be limited to this type of respirator. In another aspect of the present invention, FIG. 9 illustrates a filtering face mask respirator 310, which generally includes a mask body 312 made of a filtering material that is permeable to air and an exhalation valve assembly 320. With this type of respirator, air can be pulled into the wearer's breathing zone through the mask material of mask body 312 when the wearer inhales. The mask material should provide sufficient filtering capability to filter undesirable contaminants (such as gases and particulates) from the air entering the wearer's breathing zone when the wearer inhales. Mask body 312 has an opening 318 in the general area of a respirator wearer's mouth over which at least a portion of exhalation valve assembly 320 is positioned. Exhalation valve assembly 320 generally includes a frame 350 having an opening or orifice, a valve seat, and a valve diaphragm 352. The several components that make up the exhalation valve assembly 320 may include any of the variations and features discussed above relative to valve assembly 20. Thus, the exhalation valve assembly 320 would also operate in essentially the same manner as that described above relative to the operation of valve assembly 20.

In addition to the types of respirators described above, the valve of the present invention is intended to be useful for other types of respirator arrangements where it is desirable to provide a valve that can move from its sealed position to an open position through the breathing action of the respirator wearer, such as full facepiece respirators, powered air-purifying respirators, valved hood respirators, welding shields and other respirator arrangements. These arrangements may include one or more valves of the type contemplated by the present invention.

It is further contemplated that the valve of the present invention be used as an inhalation valve. In this arrangement, the inhalation valve assembly operates in essentially the same way as the exhalation valve, where the valve diaphragm is similarly sealed and displaced from the valve seat depending on the difference in pressure generated inside the respirator by the wearer's breathing action. In the case of an inhalation valve, however, the valve diaphragm would be facing the interior of the respirator so that it can open toward the wearer's face. Thus, inhalation by the wearer creates the necessary negative pressure inside the respirator to pull the diaphragm away from the valve seat into its open position. When the user exhales, the pressure increases inside the respirator, thereby allowing the diaphragm to move back toward its sealed position.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A undirectional valve comprising:
a valve body including a frame, a valve opening through the frame, and a valve seat extending from the frame and at least partially surrounding the valve opening; and
a valve flap having a first portion attached to the frame and an adjacent second portion free to move from a first position where the second portion is in contact with at least a part of the valve seat to a second position where at least part of the second portion is spaced from the valve seat, wherein the second portion of the valve flap comprises a first side spaced from a second side and a first end proximate the first portion and a second end spaced from the first end, wherein the valve flap further comprises a top surface and at least one rib extending from the top surface of the valve flap, and further wherein the valve flap thickness of a base part of the valve flap outside of the at least one rib decreases when moving from the first end to the second end or from the second end to the first end.

2. The unidirectional valve of claim 1, wherein the valve flap has a minimum thickness and a maximum thickness between the first and second sides, and wherein the maximum thickness is at least about 10% greater than the minimum thickness.

3. The unidirectional valve of claim 1, wherein the at least one rib provides the valve flap thickness variations between the first and second sides.

4. The unidirectional valve of claim 3, further comprising a plurality of ribs, wherein each of the plurality of ribs is spaced from each adjacent rib.

5. The unidirectional valve of claim 1, wherein the valve seat is generally planar and the valve flap has a curvature that causes a bias of the valve flap toward the valve seat to provide a seal between the valve flap and the valve seat.

6. The unidirectional valve of claim 5, wherein at least a portion of the curvature of the valve flap is at least partially flattened when the valve flap contacts the valve seat.

7. The unidirectional valve of claim 5, wherein the bias of the valve flap toward the valve seat is sufficient to provide a seal between the valve flap and the valve seat in any orientation of the unidirectional valve.

8. The unidirectional valve of claim 1, wherein the valve flap has a bottom surface that is generally planar and wherein the valve seat is generally nonplanar.

9. The unidirectional valve of claim 1, wherein the frame of the valve body includes an angled portion adjacent the valve seat.

10. The unidirectional valve of claim 1, wherein the valve is an exhalation valve.

11. The unidirectional valve of claim 1, wherein the valve is an inhalation valve.

12. The unidirectional valve of claim 1, wherein the valve flap is removably attached to the valve body.

13. A respirator having a undirectional valve, comprising;
a face mask having at least one opening for receiving a unidirectional valve; and
a unidirectional valve comprising:
a valve body including a frame, a valve opening through the frame, and a valve seat extending from the frame and at least partially surrounding the valve opening; and
a valve flap having a first portion attached to the frame and an adjacent second portion free to move from a first position where the second portion is in contact with at least a part of the valve seat to a second position where at least part of the second portion is spaced from the valve seat, wherein the second portion of the valve flap comprises a first side spaced from a second side and a first end proximate the first portion and a second end spaced from the first end, wherein the valve flap further comprises a top surface and at least one rib extending from the top surface of the valve flap, and further wherein the valve flap thickness of a base part of the valve flap outside of the at least one rib decreases when moving from the first end to the second end or from the second end to the first end.

14. The respirator of claim 13, wherein the face mask is formed of a filtering material.

15. The respirator of claim 13, wherein the unidirectional valve is an exhalation valve.

16. The respirator of claim 13, wherein the unidirectional valve is an inhalation valve.

17. A unidirectional valve comprising:
a valve body including a frame, a valve opening through the frame, and a valve seat extending from the frame and at least partially surrounding the valve opening; and
a valve flap having a first portion attached to the frame and an adjacent second portion free to move from a first position where the second portion is in contact with at least a part of the valve seat to a second position where at least part of the second portion is spaced from the valve seat, wherein the second portion of the valve flap comprises a first end proximate the first portion, a second end spaced from the first end, a top surface, a bottom surface, and at least one rib extending from the top surface of the valve flap for at least a part of the distance from the first end to the second end, and further wherein the at least one rib is in continuous contact with the top surface of the valve flap.

18. The unidirectional valve of claim 17, wherein the valve flap thickness decreases when moving from the first end to the second end or from the second end to the first end.

19. The unidirectional valve of claim 17, wherein the at least one rib comprises a plurality of ribs, wherein each of the plurality of ribs is spaced from each adjacent rib.

20. The unidirectional valve of claim 17, wherein the at least one rib extends from the first end to the second end.

21. A respirator having a unidirectional valve, comprising
a face mask having at least one opening for receiving a unidirectional valve; and
a unidirectional valve comprising:
a valve body including a frame, a valve opening through the frame, and a valve seat extending from the frame and at least partially surrounding the valve opening; and
a valve flap having a first portion attached to the frame and an adjacent second portion free to move from a first position where the second portion is in contact with at least a part of the valve seat to a second position where at least part of the second portion is spaced from the valve seat, wherein the second portion of the valve flap comprises a first end proximate the first portion, a second end spaced from the first end, a top surface, a bottom surface, and at least one rib extending from the top surface for at least a part of the distance from the first end to the second end, and further wherein the at least one rib is in continuous contact with the top surface of the valve flap.

22. The respirator of claim 21, wherein the valve flap thickness decreases when moving from the first end to the second end or from the second end to the first end.

23. The respirator of claim 21, wherein the face mask is formed of a filtering material.

24. The respirator of claim 21, wherein the unidirectional valve is an exhalation valve.

25. The respirator of claim 21, wherein the unidirectional valve is an inhalation valve.

26. A respirator having a unidirectional valve, the respirator comprising:
   a face mask comprising a valve opening; and
   a unidirectional valve located over the valve opening, the unidirectional valve comprising:
   a valve sear surrounding the valve opening; and
   a cantilevered valve flap comprising a first portion attached to the face mask outside the valve seat, the valve flap further comprising a second portion located over the valve seat, the second portion being free to move from a first position where the second portion is in contact with the valve seat to close the valve opening to a second position where at least part of the second portion is spaced from the valve seat to open the valve opening, and wherein the second portion of the valve flap comprises a first end proximate the first portion and a second end spaced from the first end, wherein the valve flap thickness decreases when moving from the first end to the second end or from the second end to the first end, and wherein the valve flap thickness is greatest proximate the first end or the second ends,
   and further wherein the valve seat is generally planar and the valve flap has a curvature that causes a bias of the valve flap against the valve seat, wherein at least a portion of the curvature of the valve flat, is at least partially flattened when the valve flat, contacts the valve seat.

27. The respirator of claim 26, wherein the second portion of the valve flap comprises at least one rib extending from the top surface for at least a part of the distance from the first end to the second end.

28. The respirator of claim 26, wherein the second portion of the valve flap comprises a first side spaced from a second side, and wherein the valve flap thinkness varies between the first and second sides.

29. The respirator of claim 26, wherein the valve flap has a minimum thickness and a maximum thickness between the first and second sides, and wherein the maximum thickness is at least about 10% greater than the minimum thickness.

30. The respirator of claim 26, wherein the bias of the valve flap toward the valve seat is sufficient to provide a seal between the valve flap and the valve seat in any orientation of the unidirectional valve.

31. A respirator having a unidirectional valve, the respirator comprising;
   a face mask comprising a valve opening; and
   a unidirectional valve located over the valve opening, the unidirectional valve comprising:
   a valve seat surrounding the valve opening; and
   a cantilevered valve flap comprising a first portion attached to the face mask outside the valve seat, the valve flap further comprising a second portion located over the valve seat, the second portion being free to move from a first position where the second portion is in contact with the valve seat to close the valve opening to a second position where at least part of the second portion is spaced from the valve seat to open the valve opening, and wherein the second portion of the valve flap comprises a first end proximate the first portion, a second end spaced from the first end, a top surface, and at least one rib extending from the top surface for at least a part of the distance from the first end to the second end,
   and further wherein the valve seat is generally planar and the valve flap has a curvature that causes a bias of the valve flap against the valve seat, wherein at least a portion of the curvature of the valve flap is at least partially flattened when the valve flap contacts the valve seat.

32. The respirator of claim 31, wherein the second portion of the valve flap comprises a first end proximate the first portion and a second end spaced from the first end, wherein the valve flap thickness decreases when moving from the first end to the second end or from the second end to the first end.

33. The respirator of claim 31, wherein the second portion of the valve flap comprises a first side spaced from a second side, and wherein the valve flap thickness varies between the first and second sides.

34. The respirator of claim 33, wherein the valve flap has a minimum thickness and a maximum thickness between the first and second sides, and wherein the maximum thickness is at least about 10% greater than the minimum thickness.

35. The respirator of claim 31, wherein the bias of the valve flap toward the valve seat is sufficient to provide a seal between the valve flap and the valve seat in any orientation of the unidirectional valve.

* * * * *

UNITED STATES PATENT AND TRADEMARK OFFICE
CERTIFICATE OF CORRECTION

PATENT NO. : 6,883,518 B2
DATED : April 26, 2005
INVENTOR(S) : Mittelstadt, William A.

It is certified that error appears in the above-identified patent and that said Letters Patent is hereby corrected as shown below:

Column 9,
Line 14, delete "unidirectional" and insert -- unidirectional -- therefore.

Column 10,
Line 1, delete "unidirectional" and insert -- unidirectional -- therefore.
Line 1, delete "comprising;" and insert -- comprising: --.
Line 56, after "comprising" insert -- : --.

Column 11,
Line 40, delete "ends," and insert -- end, -- therefore.
Lines 44 and 45, delete "flat," and insert -- flap -- therefore.

Column 12,
Line 10, delete "comprising;" and insert -- comprising: -- therefore.

Signed and Sealed this

Ninth Day of August, 2005

JON W. DUDAS
*Director of the United States Patent and Trademark Office*